United States Patent
Haran et al.

(10) Patent No.: US 9,441,961 B2
(45) Date of Patent: Sep. 13, 2016

(54) SYSTEM AND METHOD FOR CORRECTING CALIPER MEASUREMENTS OF SHEET PRODUCTS IN SHEET MANUFACTURING OR PROCESSING SYSTEMS

(75) Inventors: Frank M. Haran, North Vancouver (CA); Sebastien Tixier, North Vancouver (CA); Michael K. Y. Hughes, Vancouver (CA); Graham Duck, Vancouver (CA); John F. Shakespeare, Hiltulanlahti (FI)

(73) Assignee: Honeywell Limited, Mississauga (CA)

( * ) Notice: Subject to any disclaimer, the term of this patent is extended or adjusted under 35 U.S.C. 154(b) by 1172 days.

(21) Appl. No.: 13/460,275

(22) Filed: Apr. 30, 2012

(65) Prior Publication Data
US 2013/0289918 A1    Oct. 31, 2013

(51) Int. Cl.
| | |
|---|---|
| *G01B 5/02* | (2006.01) |
| *G01B 21/04* | (2006.01) |
| *G01B 7/06* | (2006.01) |
| *G01B 11/06* | (2006.01) |
| *G01N 33/34* | (2006.01) |

(52) U.S. Cl.
CPC .............. *G01B 21/042* (2013.01); *G01B 7/107* (2013.01); *G01B 11/0691* (2013.01); *G01N 33/346* (2013.01)

(58) Field of Classification Search
USPC ........................................... 702/85, 97, 170
See application file for complete search history.

(56) References Cited

U.S. PATENT DOCUMENTS

| | | | |
|---|---|---|---|
| 5,113,358 A | 5/1992 | Reber | |
| 5,714,763 A | 2/1998 | Chase et al. | |
| 6,281,679 B1* | 8/2001 | King et al. | 324/229 |
| 6,588,118 B2 | 7/2003 | Hellstrom | |
| 7,889,342 B2 | 2/2011 | Hellstrom et al. | |
| 2004/0172842 A1* | 9/2004 | Petrowich | 33/501.02 |
| 2006/0132808 A1 | 6/2006 | Jasinski et al. | |
| 2009/0134565 A1* | 5/2009 | Duan | B65H 23/24 271/93 |

FOREIGN PATENT DOCUMENTS

| | | |
|---|---|---|
| CA | 2 356 337 A1 | 6/2000 |
| CA | 2 460 601 A1 | 4/2003 |

(Continued)

OTHER PUBLICATIONS

Pak Hui, "Laser Caliper Sensor Model 4213", Honeywell, Jun. 2005, 36 pages.

(Continued)

*Primary Examiner* — Mohamed Charioui

(57) ABSTRACT

A method includes measuring a caliper of a sheet of material using a caliper sensor having first and second sensor modules. The method also includes adjusting the caliper measurement based on a transverse displacement between a first sensor component in the first sensor module and a second sensor component in the second sensor module to generate a corrected caliper measurement. Adjusting the caliper measurement can include applying a corrector function that adjusts the caliper measurement based on the measured transverse displacement. The corrector function can be identified by repeatedly creating misalignment between the first and second sensor components, measuring a known distance using the caliper sensor, and identifying an error between the measurement of the known distance and the known distance.

23 Claims, 7 Drawing Sheets

(56) References Cited

FOREIGN PATENT DOCUMENTS

| CA | 2 697 543 A1 | 3/2009 |
|---|---|---|
| EP | 0 449 642 A1 | 10/1991 |

OTHER PUBLICATIONS

Supplementary European Search Report dated Nov. 3, 2015 in connection with European Patent Application No. EP 13 78 4594.

* cited by examiner

SYSTEM AND METHOD FOR CORRECTING CALIPER MEASUREMENTS OF SHEET PRODUCTS IN SHEET MANUFACTURING OR PROCESSING SYSTEMS

TECHNICAL FIELD

This disclosure relates generally to measurement and control systems. More specifically, this disclosure relates to a system and method for correcting caliper measurements of sheet products in sheet manufacturing or processing systems.

BACKGROUND

Webs or other sheets of material are used in a variety of industries and in a variety of ways. These materials can include paper, multi-layer paperboard, and other products manufactured or processed in long sheets. As a particular example, long sheets of paper can be manufactured and collected in reels. These sheets of material are often manufactured or processed at high rates of speed, such as speeds of up to one hundred kilometers per hour or more.

It is often necessary or desirable to measure one or more properties of a sheet of material as the sheet is being manufactured or processed. For example, it is often desirable to measure the caliper (thickness) of a paper or other sheet being manufactured to verify whether the sheet's caliper is within certain specifications. Adjustments can then be made to the sheet-making process to ensure that the sheet's caliper stays within a desired range.

SUMMARY

This disclosure provides a system and method for correcting caliper measurements of sheet products in sheet manufacturing or processing systems.

In a first embodiment, a method includes measuring a caliper of a sheet of material using a caliper sensor having first and second sensor modules. The method also includes adjusting the caliper measurement based on a transverse displacement between the first and second sensor modules to generate a corrected caliper measurement.

In a second embodiment, a system includes a caliper sensor having first and second sensor modules configured to allow a sheet of material to pass through a gap between the sensor modules. The system also includes at least one processing unit configured to identify a caliper measurement of the sheet and to adjust the caliper measurement based on a transverse displacement between the first and second sensor modules to generate a corrected caliper measurement.

In a third embodiment, an apparatus includes at least one processing unit configured to identify a caliper measurement of a sheet of material. The at least one processing unit is also configured to adjust the caliper measurement based on a transverse displacement between first and second sensor modules of the caliper sensor to generate a corrected caliper measurement. The apparatus also includes at least one memory configured to store the corrected caliper measurement.

Other technical features may be readily apparent to one skilled in the art from the following figures, descriptions, and claims.

BRIEF DESCRIPTION OF THE DRAWINGS

For a more complete understanding of this disclosure, reference is now made to the following description, taken in conjunction with the accompanying drawings, in which.

DETAILED DESCRIPTION

FIGS. 1 through 5, discussed below, and the various embodiments used to describe the principles of the present invention in this patent document are by way of illustration only and should not be construed in any way to limit the scope of the invention. Those skilled in the art will understand that the principles of the invention may be implemented in any type of suitably arranged device or system.

Figure 1:
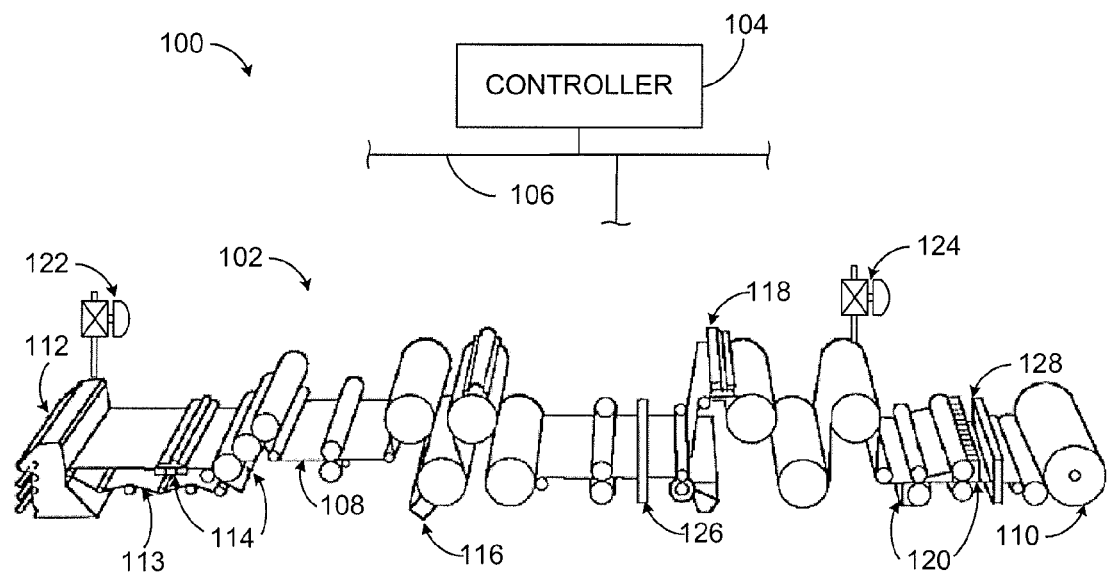
FIG. 1 illustrates an example sheet manufacturing or processing system according to this disclosure.

FIG. 1 illustrates an example sheet manufacturing or processing system 100 according to this disclosure. In this example, the system 100 includes a paper machine 102, a controller 104, and a network 106. The paper machine 102 includes various components used to produce a paper product, namely a paper sheet 108 that is collected at a reel 110. The controller 104 monitors and controls the operation of the paper machine 102, which may help to maintain or increase the quality of the paper sheet 108 produced by the paper machine 102.

In this example, the paper machine 102 includes at least one headbox 112, which distributes a pulp suspension uniformly across the machine onto a continuous moving wire screen or mesh 113. The pulp suspension entering the headbox 112 may contain, for example, 0.2-3% wood fibers, fillers, and/or other materials, with the remainder of the suspension being water. The headbox 112 may include an array of dilution actuators, which distributes dilution water into the pulp suspension across the sheet. The dilution water may be used to help ensure that the resulting paper sheet 108 has a more uniform basis weight across the sheet 108.

Arrays of drainage elements 114, such as vacuum boxes, remove as much water as possible to initiate the formation of the sheet 108. An array of steam actuators 116 produces hot steam that penetrates the paper sheet 108 and releases the latent heat of the steam into the paper sheet 108, thereby increasing the temperature of the paper sheet 108 in sections across the sheet. The increase in temperature may allow for easier removal of remaining water from the paper sheet 108. An array of rewet shower actuators 118 adds small droplets of water (which may be air atomized) onto the surface of the paper sheet 108. The array of rewet shower actuators 118 may be used to control the moisture profile of the paper sheet 108, reduce or prevent over-drying of the paper sheet 108, or correct any dry streaks in the paper sheet 108.

The paper sheet 108 is then often passed through a calendar having several nips of counter-rotating rolls. Arrays of induction heating actuators 120 heat the shell surfaces of various ones of these rolls. As each roll surface locally heats up, the roll diameter is locally expanded and hence increases nip pressure, which in turn locally compresses the paper sheet 108. The arrays of induction heating actuators 120 may therefore be used to control the caliper (thickness) profile of the paper sheet 108. The nips of a calendar may also be equipped with other actuator arrays, such as arrays of air showers or steam showers, which may be used to control the gloss profile or smoothness profile of the paper sheet.

Two additional actuators 122-124 are shown in FIG. 1. A thick stock flow actuator 122 controls the consistency of incoming stock received at the headbox 112. A steam flow actuator 124 controls the amount of heat transferred to the paper sheet 108 from drying cylinders. The actuators 122-124 could, for example, represent valves controlling the flow of stock and steam, respectively. These actuators may be used for controlling the dry weight and moisture of the paper sheet 108.

Additional components could be used to further process the paper sheet 108, such as a supercalendar (for improving the paper sheet's thickness, smoothness, and gloss) or one or more coating stations (each applying a layer of coatant to a surface of the paper to improve the smoothness and printability of the paper sheet). Similarly, additional flow actuators may be used to control the proportions of different types of pulp and filler material in the thick stock and to control the amounts of various additives (such as retention aid or dyes) that are mixed into the stock.

This represents a brief description of one type of paper machine 102 that may be used to produce a paper product. Additional details regarding this type of paper machine 102 are well-known in the art and are not needed for an understanding of this disclosure. Also, this represents one specific type of paper machine 102 that may be used in the system 100. Other machines or devices could be used that include any other or additional components for producing a paper product. In addition, this disclosure is not limited to use with systems for producing paper products and could be used with systems that process a paper product or with systems that produce or process other items or materials (such as multi-layer paperboard, cardboard, plastic, textiles, metal foil or sheets, or other or additional materials that are manufactured or processed as moving sheets).

In order to control the paper-making process, one or more properties of the paper sheet 108 may be continuously or repeatedly measured. The sheet properties can be measured at one or various stages in the manufacturing process. This information may then be used to adjust the paper machine 102, such as by adjusting various actuators within the paper machine 102. This may help to compensate for any variations of the sheet properties from desired targets, which may help to ensure the quality of the sheet 108.

As shown in FIG. 1, the paper machine 102 includes one or more scanners 126-128, each of which may include one or more sensors. Each scanner 126-128 is capable of measuring one or more characteristics of the paper sheet 108. For example, each scanner 126-128 could include sensors for measuring the anisotropy, basis weight, color, gloss, sheen, haze, surface features (such as roughness, topography, or orientation distributions of surface features), or any other or additional characteristics of the paper sheet 108.

Each scanner 126-128 includes any suitable structure or structures for measuring or detecting one or more characteristics of the paper sheet 108, such as one or more sets of sensors. The use of scanners represents one particular embodiment for measuring sheet properties. Other embodiments could be used, such as those including one or more stationary sets or arrays of sensors, deployed in one or a few locations across the sheet or deployed in a plurality of locations across the whole width of the sheet such that substantially the entire sheet width is measured.

The controller 104 receives measurement data from the scanners 126-128 and uses the data to control the paper machine 102. For example, the controller 104 may use the measurement data to adjust any of the actuators or other components of the paper machine 102. The controller 104 includes any suitable structure for controlling the operation of at least part of the paper machine 102, such as a computing device.

The network 106 is coupled to the controller 104 and various components of the paper machine 102 (such as the actuators and scanners). The network 106 facilitates communication between components of the system 100. The network 106 represents any suitable network or combination of networks facilitating communication between components in the system 100. The network 106 could, for example, represent a wired or wireless Ethernet network, an electrical signal network (such as a HART or FOUNDATION FIELDBUS network), a pneumatic control signal network, or any other or additional network(s).

Caliper measurements can be captured using one or more of the scanners 126-128. For example, one or more of the scanners 126-128 could include at least one optical caliper sensor. An optical caliper sensor can include upper and lower sensor modules, and one or more lasers or other non-contact distance measuring devices (such as chromatic confocal microscopy or terahertz devices) can be used to measure the distance to one or both sides of the sheet 108. Also, in addition to the optical measurement(s), an eddy current sensor can measure the distance between the sensor modules. A measurement coil of the eddy current sensor can be rigidly attached and referenced to one of the optical measurements. However, because of the finite size and the features of a conductive target used by the eddy current sensor, the eddy current sensor's readings can be affected by relative transverse displacement of the upper and lower sensor modules. The optical caliper sensor can therefore include additional components that measure the relative transverse displacement, and caliper measurements can be corrected using the displacement measurements. In this way, more accurate caliper measurements can be obtained, thereby enabling more precise control of the system 100.

Although FIG. 1 illustrates one example of a sheet manufacturing or processing system 100, various changes may be made to FIG. 1. For example, other systems could be used to produce other paper or non-paper products. Also, while shown as including a single paper machine 102 with various components and a single controller 104, the production system 100 could include any number of paper machines or other production machinery having any suitable structure, and the system 100 could include any number of controllers. In addition, FIG. 1 illustrates one operational environment in which the correction of caliper measurements can be used. This functionality could be used in any other suitable system.

FIGS. 2A through 2G illustrate a first example caliper sensor 200 in a sheet manufacturing or processing system according to this disclosure. The caliper sensor 200 could, for example, be used in one or more of the scanners 126-128 shown in FIG. 1.

Figure 2A:
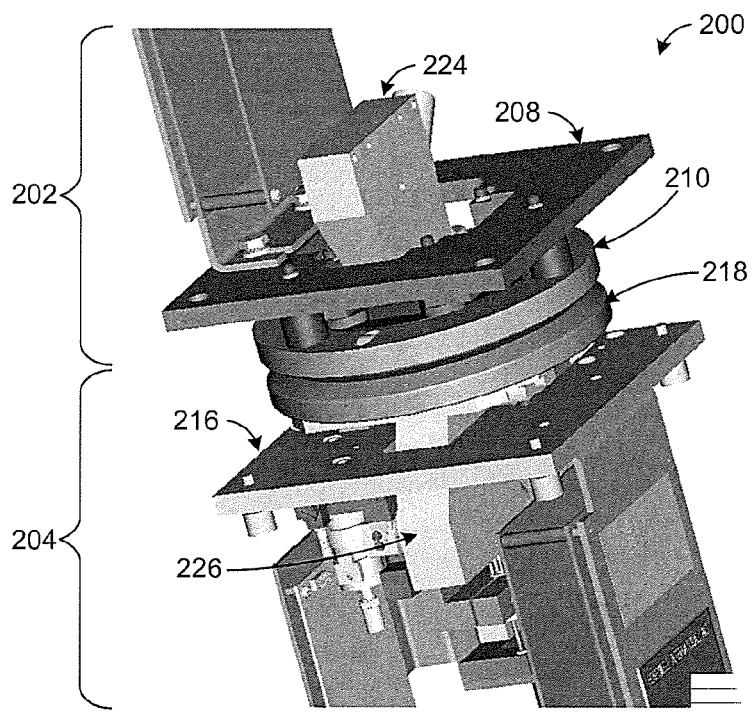
FIGS. 2A through 2G illustrate a first example caliper sensor in a sheet manufacturing or processing system according to this disclosure.
Figure 2B:
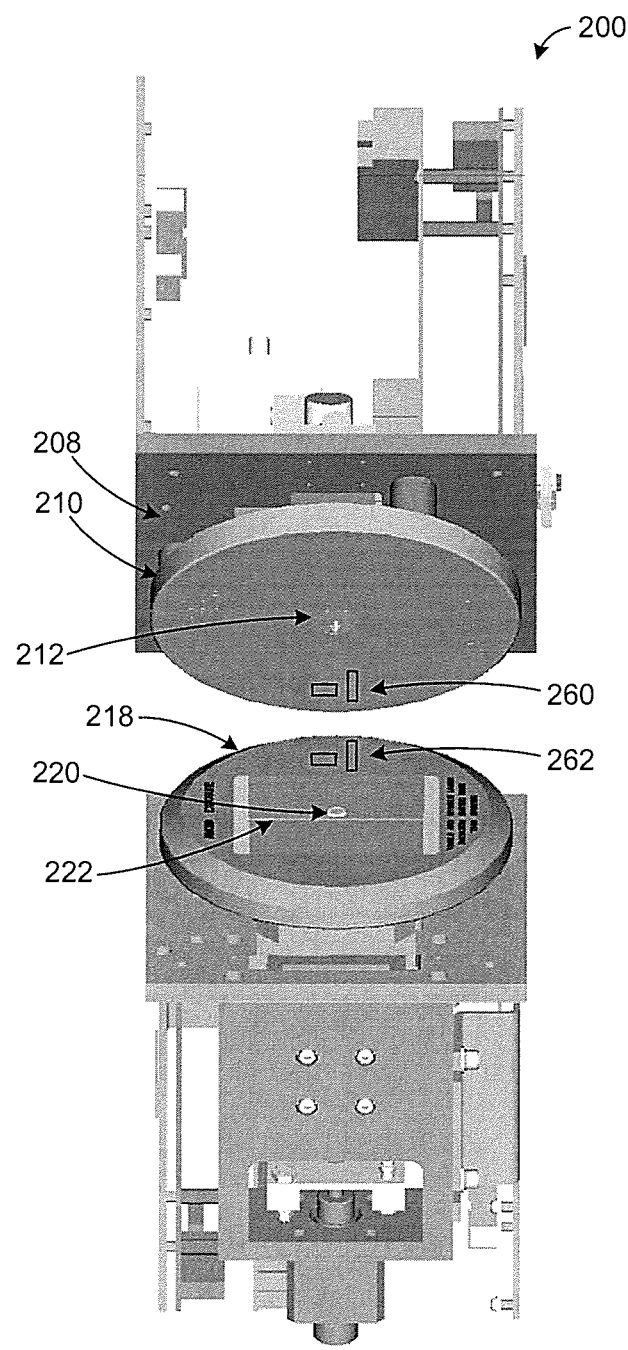

As shown in FIG. 2A, the caliper sensor 200 includes an upper sensor module 202 and a lower sensor module 204. The upper sensor module 202 in this example includes an upper sensor baseplate 208, which can be used to physically couple the upper sensor module 202 to another structure (such as a sensor platform that moves the upper sensor module 202 across a surface of the sheet 108). Other components of the upper sensor module 202 could also be mounted or otherwise coupled to the upper sensor module 202. A sensor dust cover 210 denotes a structure that is placed near the sheet 108. The sensor dust cover 210 includes an aperture 212 as shown in FIG. 2B. The aperture 212 allows radiation to pass through the dust cover 210, either from a radiation source for delivery to the sheet 108 or to a detector after interaction with the sheet 108.

The lower sensor module 204 includes a lower sensor baseplate 216 and a lower sensor dome 218. The lower sensor baseplate 216 can be used to physically couple the lower sensor module 204 to another structure (such as a sensor platform that moves the lower sensor module 204 across another surface of the sheet 108). Other components of the lower sensor module 204 could also be mounted or otherwise coupled to the lower sensor module 204. The lower sensor dome 218 serves various functions, such as providing a target for an eddy current sensor (Z-sensor 227 as described below) and acting as a sheet stabilizer. The sheet 108 passes through a gap between the upper and lower sensor modules 202-204. The lower sensor dome 218 includes an aperture 220 as shown in FIG. 2B. The lower sensor dome 218 also includes a sheet positioning structure 222 for helping to maintain the position of the sheet 108 when the sheet 108 passes between the sensor modules 202-204. For example, the structure 222 could include a Coanda backstep.

Each sensor module 202-204 includes any suitable structure for placement near a sheet and for facilitating caliper measurements of the sheet. Each sensor baseplate 208, 216 includes any suitable structure for physically coupling a sensor module to an external structure (such as a sensor platform). Each aperture 212, 220 represents any suitable opening or other mechanism allowing passage of radiation through a sensor module. The sheet positioning structure 222 includes any suitable structure that helps to maintain the position of a sheet.

In this example, a distance measurement unit 224 is mounted to the upper sensor baseplate 208 via another component (the Z-sensor 227), and a distance measurement unit 226 is mounted to the lower sensor baseplate 216. The distance measurement units 224-226 perform non-contact distance measuring operations to measure distance to opposing sides of the sheet 108. For example, each distance measurement unit 224-226 could generate radiation that is provided to the sheet 108. Each distance measurement unit 224-226 could also measure radiation that has interacted with the sheet 108. Each distance measurement unit 224-226 could further perform triangulation or other operations to measure distance, or it could provide its data to an external component that performs triangulation or other operations to measure distance.

Each distance measurement unit 224-226 includes any suitable structure for measuring distance in a non-contact manner. For instance, each distance measurement unit 224-226 could include a laser for generating radiation and a position-sensitive detector with associated electronics and optics to make a triangulation measurement. In some embodiments, one distance measurement unit generates radiation in the visible spectrum, and another distance measurement unit generates radiation in the infrared spectrum.

Figure 2C:
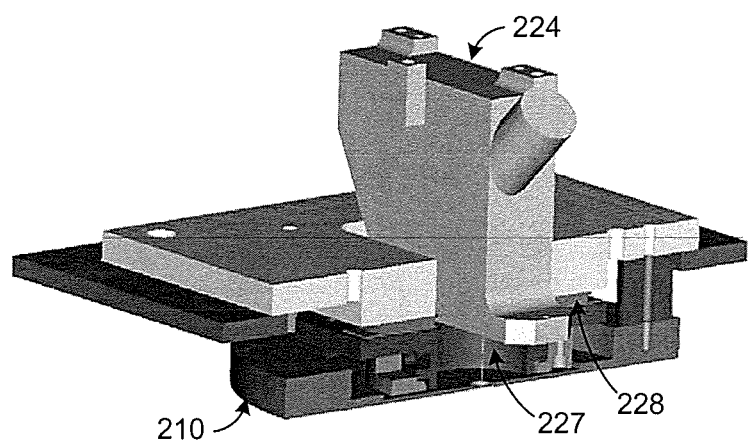

FIG. 2C illustrates additional details of portions of the upper sensor module 202. As shown here, the distance measurement unit 224 is mounted to the Z-sensor 227, which in turn is mounted to the upper sensor baseplate 208. The upper sensor module 202 also includes a cooler 228. The Z-sensor 227 includes a sensing coil for an eddy current sensor or an inductive proximity sensor and measures the distance to the lower sensor dome 218. As described below, this distance is used to determine the caliper of the sheet 108. The Z-sensor 227 includes any suitable structure for wirelessly measuring distance, such as an inductive sensor coil that generates eddy current in the sensor dome 218. The cooler 228 helps to maintain the temperature of the Z-sensor 227. The cooler 228 includes any suitable structure for cooling a structure, such as a Peltier cooler.

Figure 2D:
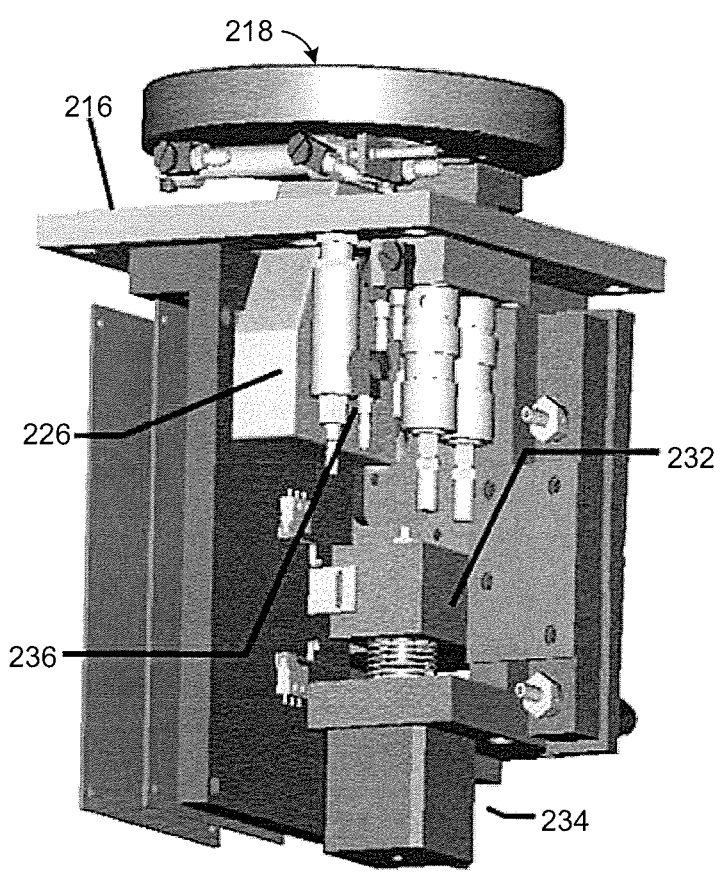

FIG. 2D illustrates additional details of portions of the lower sensor module 204. As shown here, the distance measurement unit 226 is mounted on the lower sensor baseplate 216. The lower sensor module 204 also includes a movable stage that can move the sensor dome 218. Movement of the sensor dome 218 can be used during calibration and other operations involving the Z-sensor 227. In particular, the Z-sensor 227 creates eddy currents in the sensor dome 218, and precise positioning of the sensor dome 218 can be performed using the movable stage.

In this example, a precision slide 232 moves the sensor dome 218 and is actuated by a stepper motor 234. A sensor 236 measures the movement of the sensor dome 218, such as with sub-micron precision. The sensor dome 218 includes any suitable conductive structure supporting operation of a Z-sensor. The precision slide 232 includes any suitable structure for moving an eddy current sensor's target. The motor 234 includes any suitable structure for moving a precision slide to thereby move an eddy current sensor's target. The sensor 236 includes any suitable structure for measuring a position of an eddy current sensor's target, such as a linear variable differential transformer or a high precision optical encoder.

Figure 2E:
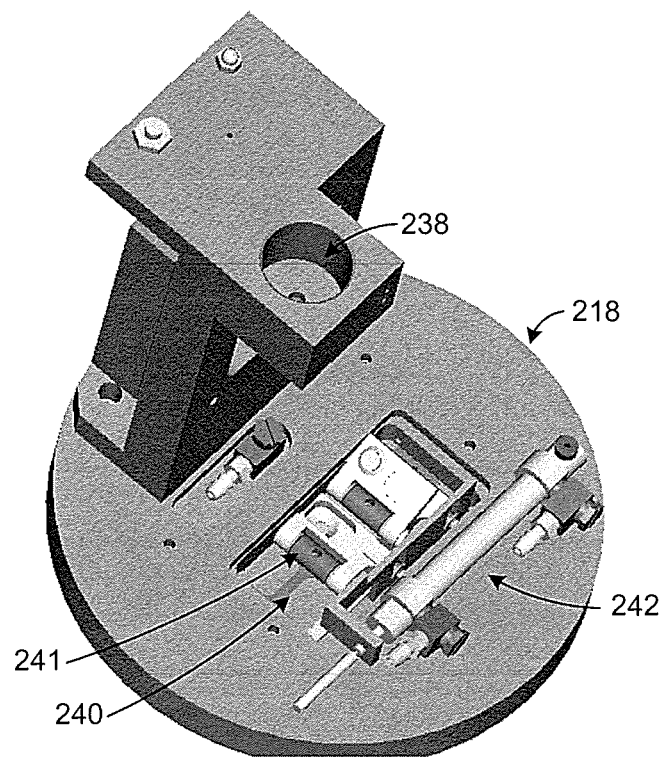

FIG. 2E illustrates additional details of portions of the sensor dome 218. Here, the sensor dome 218 includes a mount 238, which represents any suitable structure for coupling the sensor dome 218 to the precision slide 232. The sensor dome 218 also includes at least one holder 240. The holder 240 includes any suitable structure for holding a flag 241. During normal operation, the holder 240 is moved so that nothing is located in the aperture 220, allowing radiation to pass from the distance measurement unit 226 towards the sheet 108 and/or from the sheet 108 to the distance measurement unit 226. During standardization or recalibration operations, the holder 240 is moved so that a flag 241 is located in the aperture 220. The flag 241 represents a structure having one or more known characteristics, such as reflectivity. The flag 241 helps to calibrate the operation of the caliper sensor's components.

Figure 2F:
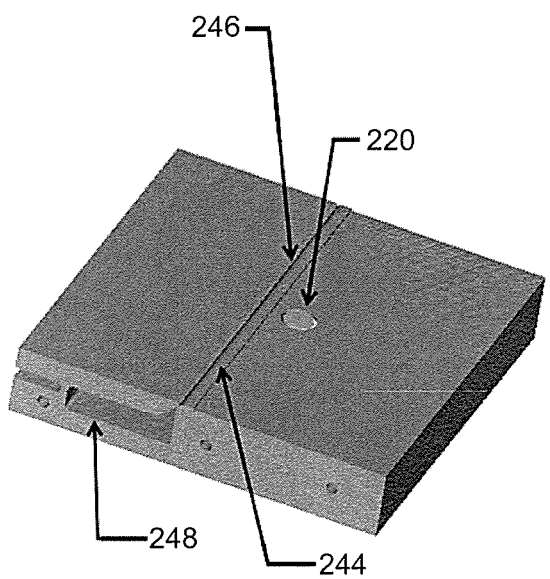

FIG. 2F illustrates other additional details of portions of the lower sensor module 204. In FIG. 2F, the aperture 220 provides access to a flag 241 within the holder 240. The lower sensor module 204 also includes a backstep 244, which represents a bumped or raised surface of the lower sensor dome 218. A slot 246 is next to the backstep 244 and leads into an air plenum 248. These structures 244-248 help to stabilize the sheet 108 in the gap between the sensor modules 202-204.

Figure 2G:
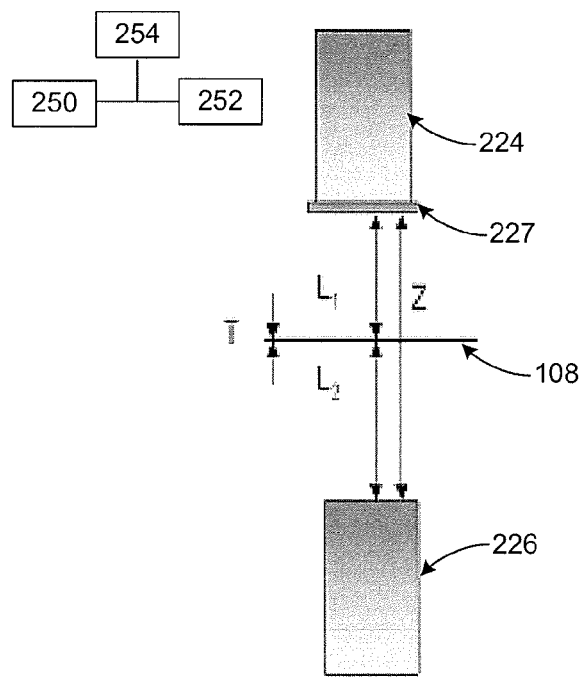

FIG. 2G illustrates an example of how the caliper sensor 200 operates to measure the thickness of the sheet 108. In this example, the Z-sensor 227 measures the distance Z between the sensor modules 202-204. Also, the caliper sensor 200 measures the distance $L_1$ between the sensor module 202 and the sheet 108 using the distance measurement unit 224, and the caliper sensor 200 measures the distance $L_2$ between the sensor module 204 and the sheet 108 using the distance measurement unit 226. The caliper (thickness) T of the sheet 108 can then be calculated by computing $Z-L_1-L_2$. In some embodiments, the calculation of the caliper can be done using at least one processing unit 250, such as a microprocessor, microcontroller, digital signal processor, application specific integrated circuit, field programmable gate array, or other computing or processing device. At least one memory 252 can store instructions and data used, generated, or collected by the processing unit(s) 250. At least one network interface 254 can be used to communicate with external devices or systems, such as to transmit caliper measurements to the controller 104 or other destination(s).

Figure 3A:
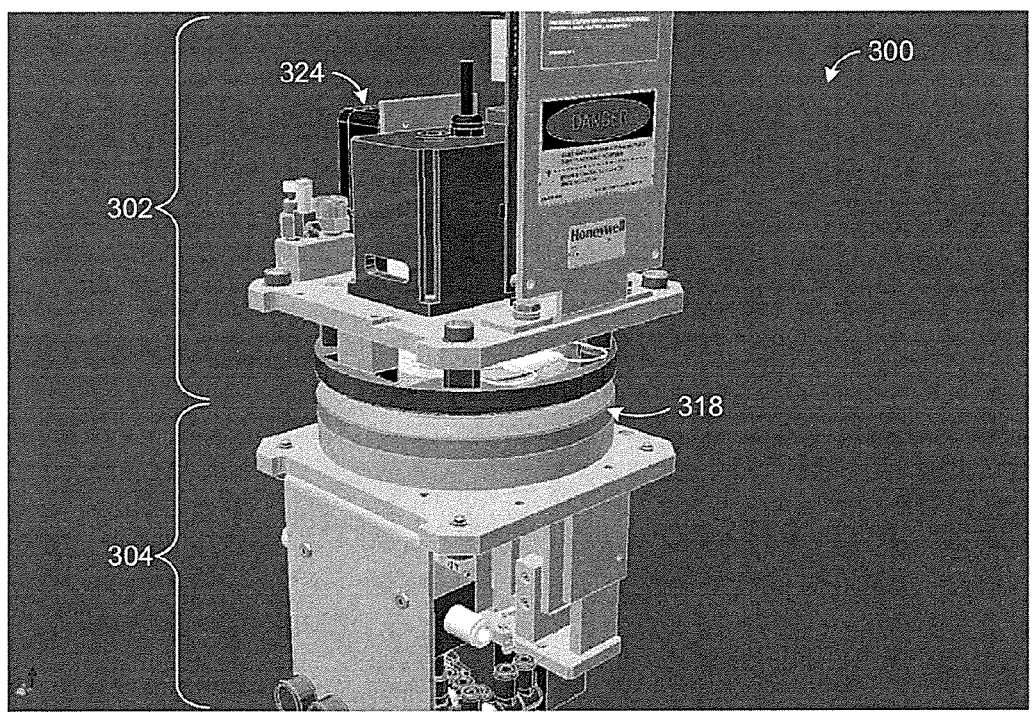
FIGS. 3A through 3C illustrate a second example caliper sensor in a sheet manufacturing or processing system according to this disclosure.
Figure 3B:
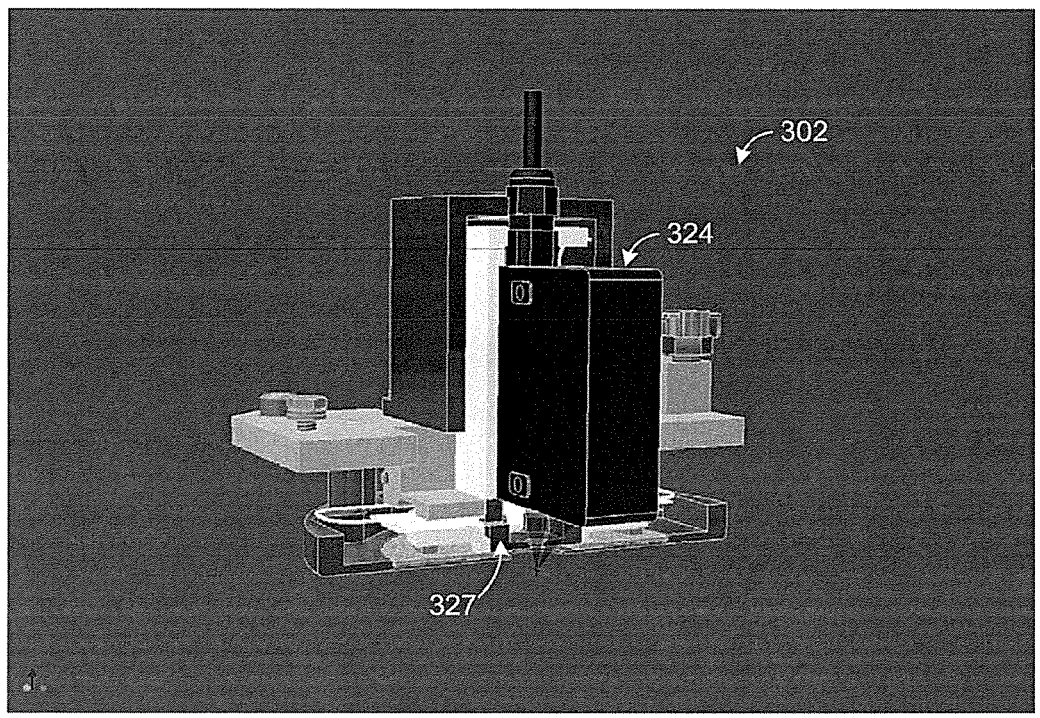
Figure 3C:
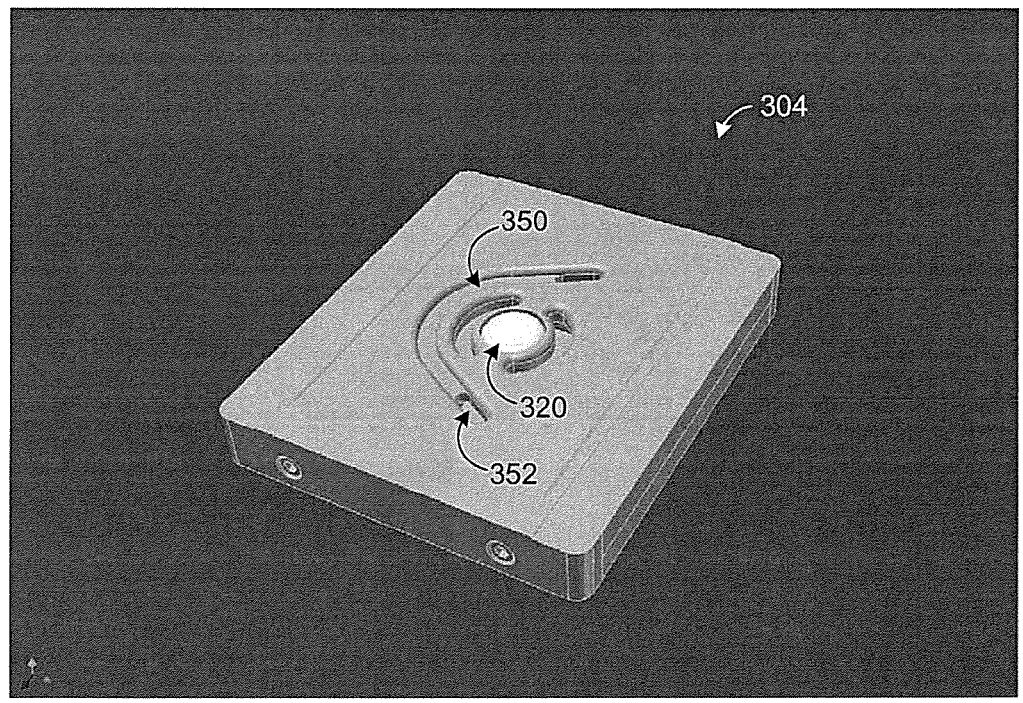

FIGS. 3A through 3C illustrate a second example caliper sensor 300 in a sheet manufacturing or processing system according to this disclosure. The caliper sensor 300 here operates to measure the distance on one side of the sheet 108, while the other side of the sheet 108 physically contacts the caliper sensor 300. This allows a caliper measurement to occur using only one triangulation or other distance calculation.

In this example, the caliper sensor 300 includes an upper sensor module 302 and a lower sensor module 304. Portions of the upper sensor module 302 are shown in FIG. 3B, and a portion of the lower sensor module 304 is shown in FIG. 3C. As shown here, the upper sensor module 302 includes a distance measurement unit 324, which measures a distance from the upper sensor module 302 to the sheet 108. The distance measurement unit 324 could, for example, direct a laser beam or other radiation at the sheet 108, receive reflected radiation from the sheet 108, and triangulate the sheet's distance. A Z-sensor 327 calculates a distance to a lower sensor dome 318 in the lower sensor module 304. A cooler could be used to help maintain the temperature of the Z-sensor 327. The lower sensor dome 318 helps to stabilize the sheet 108 and acts as a target for the Z-sensor 327.

As shown in FIG. 3C, the lower sensor module 304 includes a button 320, which protrudes slightly from the sensor module 304. During normal operation, the sheet 108 could contact the button 320 during caliper measurements. During standardization or recalibration operations, the distance measurement unit 324 could direct radiation at the button 320, which reflects the radiation back towards the distance measurement unit 324. The button 320 includes any suitable structure supporting reflection of radiation, such as a structure containing a fixed or movable flag.

The lower sensor module 304 also includes various channels 350 adjacent to the button 320. At least some of the channels 350 include passages 352. During operation, one or more suction devices could be fluidly coupled to the lower sensor module 304, and the suction devices could remove air from the channels 350 through the passages 352. This can be done to remove boundary layer air moving with the sheet 108, which can help to stabilize the sheet 108. Any suitable suction device(s) could be used here. Also, the channels 350 could have any suitable size, shape, dimensions, and arrangement, and any suitable passages 352 could be used.

In the example shown in FIGS. 3A through 3C, the sheet 108 physically contacts the button 320, which is physical attached to the sensor dome 318. The channels 350 and passages 352 support stabilization of the sheet 108 and help to hold the sheet 108 against the button 320. During calibration, the distance between the upper sensor module 302 and the button 320 can be determined. Thus, to calculate the sheet's caliper during caliper measurements, the distance between the upper sensor module 302 and the sheet 108 can be subtracted from the distance between the upper sensor module 302 and the button 320.

The caliper sensor 300 could otherwise contain many of the elements shown in FIGS. 2A through 2G. For example, the lower sensor module 304 could include a precision slide 232, a stepper motor 234, and a sensor 236 for moving the sensor dome 318.

As noted above, the Z-sensors 227, 327 use eddy currents to measure the distance between upper and lower sensor modules in a caliper sensor. For example, these eddy currents are created in the Z-sensor's target (sensor dome 218, 318) by the coil of the Z-sensor 227, 327. As shown in FIG. 2G, this distance Z along with the distances $L_1$ and $L_2$ (measured by the distance measurement units 224-226, respectively) allow the caliper sensor 200 to calculate the thickness T of the sheet 108. A similar calculation can occur in the caliper sensor 300, where the distance Z along with the distance $L_1$ allow the caliper sensor 300 to calculate the thickness T of the sheet 108 (the distance $L_2$ is assumed to be zero).

A problem can arise when the upper and lower sensor modules in a caliper sensor are not aligned in the x and y directions. The x direction could represent the direction across the width of the sheet 108 (also known as the "cross direction" or CD). The y direction could represent the direction down the length of the sheet 108 (also known as the "machine direction" or MD). When there is misalignment in the x and/or y directions, the Z-sensor 227, 327 in the upper sensor module is not precisely aligned with its target (sensor dome 218, 318) in the lower sensor module. This can decrease the precision of the caliper measurements taken using the caliper sensor 200, 300.

In accordance with this disclosure, a caliper sensor includes a mechanism for identifying displacement between its upper and lower sensor modules or otherwise identifying displacement between components of a Z-sensor (such as misalignment between a coil and its target). The displacement can be measured in the x-y plane, which may be on or parallel to the expected location of the sheet 108. Note that the displacement can be measured or expressed in any suitable manner. For example, the displacement could be measured or expressed using x and y distances in a Cartesian coordinate system, distance and angle in a polar coordinate system, or in any other suitable manner.

By varying the displacement, it is possible to characterize how different displacements cause errors in the Z-sensor measurements (and therefore errors in the caliper measurements). For example, varying the displacement in the x direction and/or the y direction could be done to identify a linear, quadratic, or other formula that defines the caliper error caused by the displacement. During normal operation, measurements of the actual displacement could then be used in the formula to identify the actual error in the caliper measurements. This error could be used to generate corrected caliper measurements, which are closer to the actual thickness of the sheet 108.

Any suitable technique could be used to create misalignment in the sensor modules of a caliper sensor in order to characterize the error caused by misalignment. Also, any suitable technique could be used to measure actual misalignment in the sensor modules of a caliper sensor. For example, in some embodiments, one or more additional sensors are used to measure the displacement between the sensor modules. An example of this is shown in FIG. 2B, where sensors 260 and/or sensors 262 are used to identify the displacement. The sensors 260 can be rigidly attached to the upper sensor module, and/or the sensors 262 can be rigidly attached to the lower sensor module. These sensors 260, 262 measure the relative transverse displacement between the upper and lower sensor modules (in x and y or other measurements). The sensors 260, 262 include any suitable structure(s) for measuring displacement, such as magneto-resistive sensors like HMC1501 displacement sensors from HONEYWELL INTERNATIONAL INC.

The characteristic sensitivity of a caliper sensor to misalignment can be determined at any suitable time(s), such as in a factory or in situ during operation of the caliper sensor in a sheet manufacturing or processing system. This characteristic sensitivity can then be used along with an actual displacement measurement to identify the error induced by the actual displacement. Additional details regarding the determination and use of misalignment correction are provided below.

Although FIGS. 2A through 3C illustrate example caliper sensors in a sheet manufacturing or processing system, various changes may be made to FIGS. 2A through 3C. For example, each component shown in these figures could have any suitable size, shape, and dimensions and can be formed from any suitable material(s). Also, one or more components shown in these figures could be omitted if the functions associated with those components are not needed. In addition, the use of misalignment correction can be done with any other suitable caliper sensor and is not limited to use with just the caliper sensors 200, 300 shown here.

Figure 4:
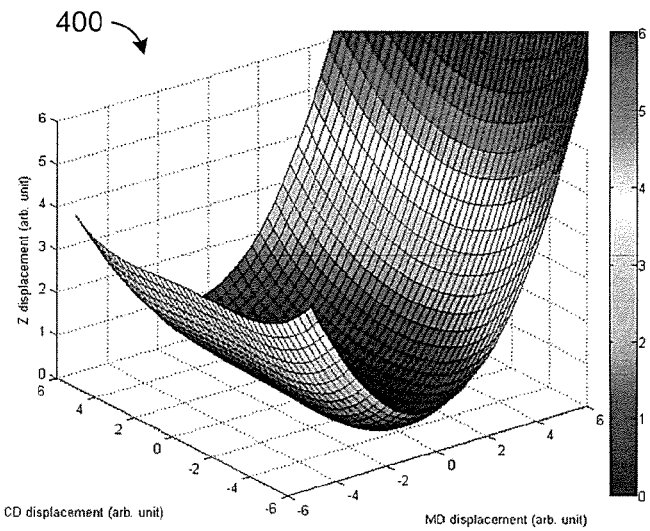
FIG. 4 illustrates an example relationship between caliper measurement error and sensor module displacement according to this disclosure.

FIG. 4 illustrates an example relationship between caliper measurement error and sensor module displacement according to this disclosure. In particular, FIG. 4 illustrates an example characteristic sensitivity 400 of a caliper sensor to misalignment.

As shown in FIG. 4, misalignment in the CD direction is plotted along one of the lower axes, and misalignment in the MD direction is plotted along another of the lower axes. The error resulting from misalignment in the MD and CD directions in plotted along the vertical axis. The characteristic sensitivity 400 shown in FIG. 4 could be generated by altering the alignment of a caliper sensor and detecting an error in the measurement of a known distance. Repeating this process over a number of different MD and CD misalignment combinations can be used to generate the characteristic sensitivity 400.

Note that caliper error could be symmetric or asymmetric in the MD and CD directions. Also note that caliper error in the MD and CD directions are jointly represented here as a common surface, but they could be represented separately. Further note that while the surface here is shown in Cartesian form, spherical or other forms could be used. In addition, note that the nominal operating x and y values need not be at an extremum, inflection, or other point of local symmetry or anti-symmetry in either the CD or MD axis.

Although FIG. 4 illustrates one example of a relationship between caliper measurement error and sensor module displacement, various changes may be made to FIG. 4. For example, the characteristic sensitivity 400 shown in FIG. 4 may be specific to one particular caliper sensor or type of caliper sensor. Other caliper sensors could be other characteristic sensitivities.

Figure 5:
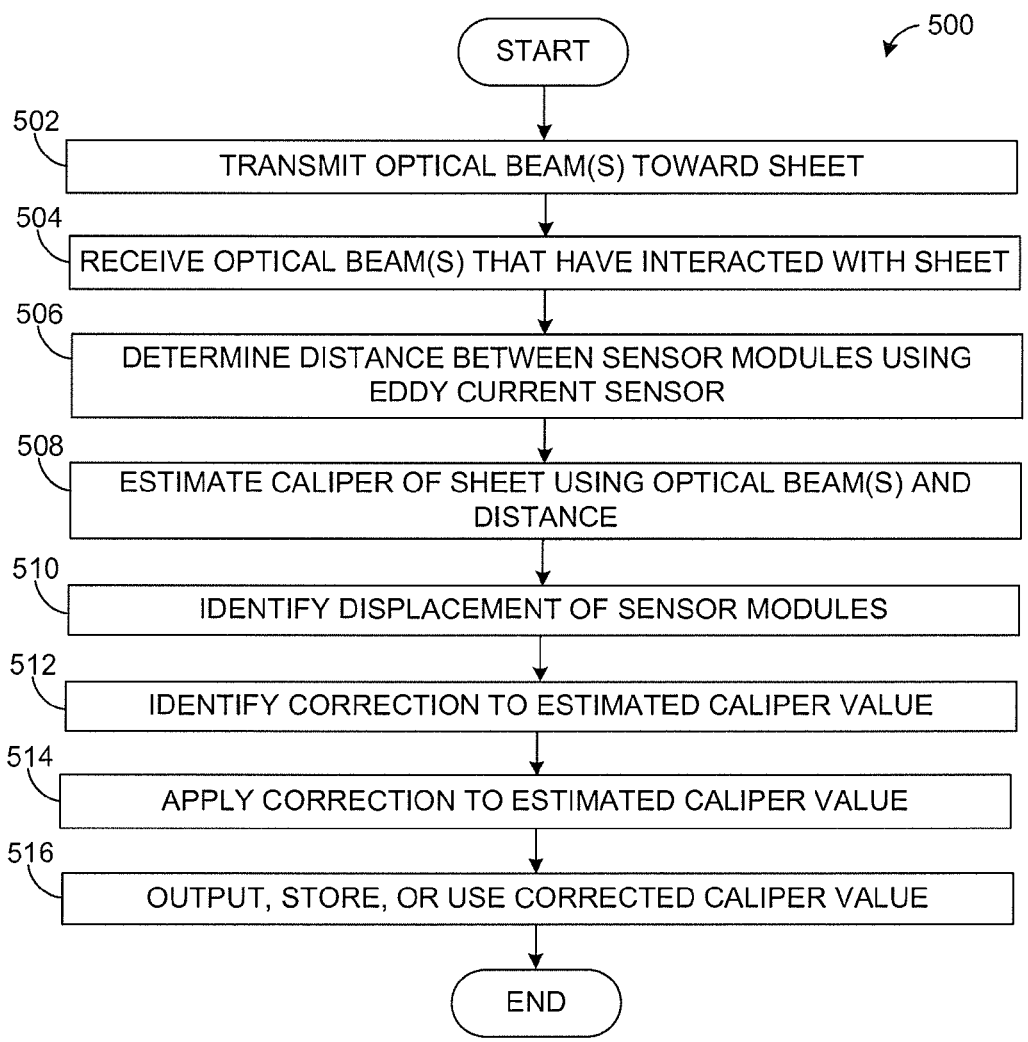
FIG. 5 illustrates an example method for caliper measurement in a sheet manufacturing or processing system according to this disclosure.

FIG. 5 illustrates an example method 500 for caliper measurement in a sheet manufacturing or processing system according to this disclosure. As shown in FIG. 5, one or more optical beams are transmitted towards a sheet at step 502, and one or more optical beams that have interacted with the sheet are received at step 504. This could include, for example, the distance measurement units 224-226 transmitting laser beams towards both sides of the sheet 108. This could also include the distance measurement unit 324 transmitting a laser beam towards only one side of the sheet 108. This can further include one or more detectors in the distance measurement unit(s) on one or both sides of the sheet 108 receiving one or more laser beams that have reflected off the sheet 108.

The distance between two sensor modules is determined using an eddy current sensor at step 506. This could include, for example, using the Z-sensor 227, 327 to identify the distance between two sensor modules 202-204, 302-304. As a particular example, eddy currents created in the Z-sensor's target (sensor dome 218, 318) by an oscillating current in the Z-sensor's coil can be detected by the same Z-sensor coil, and this detected response identifies the distance between the sensor modules. The caliper of the sheet is estimated using the optical beam(s) and estimated distance at step 508. This could include, for example, the caliper sensor subtracting one or more distances estimated using the optical beam(s) from the Z-sensor's calculated distance.

The current displacement of the sensor modules in the caliper sensor is identified at step 510. This could include, for example, the caliper sensor using sensors 260 and/or 262 to measure the current displacement between the sensor modules. Based on the identified misalignment, a correction to the estimated caliper value is identified at step 512, and the correction is applied to the estimated caliper value to generate a corrected caliper value at step 514. This could include, for example, the processing unit 250 in the caliper sensor using the measured misalignment to identify a correction to be made to the estimated caliper measurement. As a particular example, the processing unit 250 in the caliper sensor could use the following equation to identify a corrected caliper measurement:

$$t_{cor} = t_{uncor} + x \times \frac{dt}{dx} + y \times \frac{dt}{dy} + z \times \frac{dt}{dz} \tag{1}$$

where $t_{uncor}$ represents an uncorrected caliper measurement and $t_{cor}$ represents a corrected caliper measurement. Also, x and y represent the current misalignment between the sensor modules, and z represents the measured Z-distance between the sensor modules. In addition, dt/dx, dt/dy, and dt/dz denote correction factors in the x, y, and z directions. In some embodiments, dt/dz could be quite small, so the processing unit 250 in the caliper sensor could use the following equation to identify a corrected caliper measurement:

$$t_{cor} \approx t_{uncor} + x \times \frac{dt}{dx} + y \times \frac{dt}{dy} \tag{2}$$

Note that these equations are for illustration only and other equations (such as quadratic formulas) could be used.

The corrected caliper measurement could be output, stored, or used in some manner at step 516. This could include, for example, the processing unit 250 in the caliper sensor outputting the corrected caliper measurement to the controller 104 for use in adjusting the sheet manufacturing or processing system. This could also include the caliper sensor providing the corrected caliper measurement to a historian or other database for short-term or long-term storage. The corrected caliper measurement could be used in any other suitable manner.

The equation(s) used in step 512 to identify the correction to the estimated caliper measurement can be determined in any suitable manner. For example, in some embodiments, in situ measurements can be taken using at least one flag 241 in a holder 240 with artificially created misalignment of the sensor modules. The in situ measurements can then be used to generate at least one fitted corrector function, such as by identifying values of dt/dx, dt/dy, and possibly dt/dz. The corrector function(s) can be used to calculate a correction for an estimated caliper measurement using actual misalignment of the sensor modules.

In other embodiments, at least one corrector function is generated for a caliper sensor in the factory and stored (such as in the memory 252). In situ measurements can then be taken after installation of the caliper sensor using at least one flag 241 in a holder 240 to fit the corrector function to initial displacement measurements for that caliper sensor. At that point, the corrector function is fitted to the caliper sensor and is used to correct caliper measurements based on actual misalignment of the sensor modules.

In still other embodiments, at least one corrector function is generated for multiple caliper sensors in the factory and stored in each caliper sensor (such as in each sensor's memory 252). In situ measurements can then be taken after installation of each caliper sensor using at least one flag 241 in a holder 240 to fit the corrector function to initial displacement measurements for that particular caliper sensor. At that point, the corrector function is fitted to the particular caliper sensor and is used to correct caliper measurements based on actual misalignment of the sensor modules in that caliper sensor.

Note that any other suitable technique could be used to generate at least one corrector function for a caliper sensor. Also note that any suitable corrector function(s) could be generated. For example, Equation (1) or (2) could be generated by identifying the values of dt/dx, dt/dy, and possibly dt/dz. These values can vary depending on the specific caliper sensor or type of caliper sensor being analyzed. As a specific example for a particular caliper sensor, dt/dx could represent a function that varies from about −1.5 μm to about 1.5 μm per millimeter in the caliper. Also, dt/dy could represent a linear function that varies from about −10 μm to about 10 μm per millimeter in the caliper. In addition, dt/dz could be relatively constant at about 1 μm per millimeter in the caliper. In other embodiments, a quadratic correction function such as the one shown below could be calculated:

$$t_{cor} \approx t_{uncor} + C_1 \times (x + \text{OffsetCD})^2 + C_2 \times (y + \text{OffsetMD}) \quad (3)$$

where $C_1$ and $C_2$ represent constants and OffsetCD and OffsetMD denote offset values. Any other suitable corrector functions could be used.

Although FIG. 5 illustrates one example of a method 500 for caliper measurement in a sheet manufacturing or processing system, various changes may be made to FIG. 5. For example, while shown as a series of steps, various steps in FIG. 5 could overlap, occur in parallel, occur in a different order, or occur multiple times.

In some embodiments, various functions described above are implemented or supported by a computer program that is formed from computer readable program code and that is embodied in a computer readable medium. The phrase "computer readable program code" includes any type of computer code, including source code, object code, and executable code. The phrase "computer readable medium" includes any type of medium capable of being accessed by a computer, such as read only memory (ROM), random access memory (RAM), a hard disk drive, a compact disc (CD), a digital video disc (DVD), or any other type of memory.

It may be advantageous to set forth definitions of certain words and phrases used throughout this patent document. The term "couple" and its derivatives refer to any direct or indirect communication between two or more elements, whether or not those elements are in physical contact with one another. The terms "application" and "program" refer to one or more computer programs, software components, sets of instructions, procedures, functions, objects, classes, instances, related data, or a portion thereof adapted for implementation in a suitable computer code (including source code, object code, or executable code). The terms "transmit," "receive," and "communicate," as well as derivatives thereof, encompass both direct and indirect communication. The terms "include" and "comprise," as well as derivatives thereof, mean inclusion without limitation. The term "obtain" and its derivatives refer to any acquisition of data or other tangible or intangible item, whether acquired from an external source or internally (such as through internal generation of the item). The term "or" is inclusive, meaning and/or. The phrases "associated with" and "associated therewith," as well as derivatives thereof, may mean to include, be included within, interconnect with, contain, be contained within, connect to or with, couple to or with, be communicable with, cooperate with, interleave, juxtapose, be proximate to, be bound to or with, have, have a property of, or the like. The term "controller" means any device, system, or part thereof that controls at least one operation. A controller may be implemented in hardware, firmware, software, or some combination of at least two of the same. The functionality associated with any particular controller may be centralized or distributed, whether locally or remotely.

While this disclosure has described certain embodiments and generally associated methods, alterations and permutations of these embodiments and methods will be apparent to those skilled in the art. Accordingly, the above description of example embodiments does not define or constrain this disclosure. Other changes, substitutions, and alterations are also possible without departing from the spirit and scope of this disclosure, as defined by the following claims.

What is claimed is:

1. A method comprising:
   measuring a caliper of a sheet of material using a caliper sensor having first and second sensor modules; and
   adjusting the caliper measurement based on a transverse displacement between a first sensor component in the first sensor module and a second sensor component in the second sensor module to generate a corrected caliper measurement;
   wherein the first sensor module comprises:
     a first radiation source configured to direct first radiation towards a first side of the sheet;
     a cover having a first aperture configured to allow the first radiation to pass through the cover; and
     a Z-sensor configured to measure distance to the second sensor module;
   wherein the second sensor module comprises:
     a second radiation source configured to direct second radiation towards a second side of the sheet;
     a dome having a second aperture configured to allow the second radiation to pass through the dome, the dome providing a target for the Z-sensor; and
     at least one holder configured to position at least one flag within the second aperture during standardization or calibration of the caliper sensor, the at least one flag having one or more known characteristics; and wherein the caliper of the sheet is measured using measurements of the first and second radiation that have interacted with the sheet.

2. The method of claim 1, further comprising:
measuring the transverse displacement between the first and second sensor components using at least one displacement sensor.

3. The method of claim 2, wherein adjusting the caliper measurement comprises applying a corrector function that adjusts the caliper measurement based on the measured transverse displacement.

4. The method of claim 3, wherein the corrector function comprises one of a linear function and a quadratic function.

5. The method of claim 3, further comprising:
identifying the corrector function by repeatedly creating misalignment between the first and second sensor components, measuring a known distance using the caliper sensor, and identifying an error between the measurement of the known distance and the known distance.

6. The method of claim 1, wherein the second sensor module further comprises:
a precision slide configured to move the dome;
a stepper motor configured to move the precision slide in order to move the dome; and
a sensor configured to measure movement of the dome.

7. The method of claim 2, wherein measuring the transverse displacement comprises measuring the transverse displacement in a first direction across a width of the sheet and in a second direction along a length of the sheet.

8. The method of claim 1, wherein measuring the caliper of the sheet comprises:
measuring a first distance between the first and second sensor modules;
measuring at least one second distance from at least one of the sensor modules to the sheet; and
subtracting the at least one second distance from the first distance.

9. The method of claim 1, further comprising:
adjusting operation of a sheet manufacturing or processing system based on the corrected caliper measurement.

10. A system comprising:
a caliper sensor comprising first and second sensor modules configured to allow a sheet of material to pass through a gap between the sensor modules; and
at least one processing unit configured to identify a caliper measurement of the sheet, the at least one processing unit also configured to adjust the caliper measurement based on a transverse displacement between a first sensor component in the first sensor module and a second sensor component in the second sensor module;
wherein the first sensor module comprises:
a first radiation source configured to direct first radiation towards a first side of the sheet;
a cover having a first aperture configured to allow the first radiation to pass through the cover; and
a Z-sensor configured to measure distance to the second sensor module;
wherein the second sensor module comprises:
a second radiation source configured to direct second radiation towards a second side of the sheet;
a dome having a second aperture configured to allow the second radiation to pass through the dome, the dome providing a target for the Z-sensor; and
at least one holder configured to position at least one flag within the second aperture during standardization or calibration of the caliper sensor, the at least one flag having one or more known characteristics; and
wherein the at least one processing unit is configured to identify the caliper measurement of the sheet using measurements of the first and second radiation that have interacted with the sheet.

11. The system of claim 10, wherein the at least one processing unit is configured to identify the transverse displacement between the first and second sensor components using one or more measurements from at least one displacement sensor.

12. The system of claim 11, wherein the at least one processing unit is configured to adjust the caliper measurement by applying a corrector function that adjusts the caliper measurement based on the identified transverse displacement.

13. The system of claim 12, wherein the at least one processing unit is further configured to identify the corrector function.

14. The system of claim 11, wherein the transverse displacement comprises a transverse displacement between a sensor coil of the Z-sensor in the first sensor module and a conductive sensor target of the dome in the second sensor module.

15. The system of claim 10, wherein the at least one processing unit is configured to identify the caliper measurement by:
determining a first distance between the first and second sensor modules;
determining at least one second distance from at least one of the sensor modules to the sheet; and
subtracting the at least one second distance from the first distance.

16. The system of claim 10, wherein:
the at least one processing unit is configured to obtain measurements of the first radiation that has interacted with the at least one flag during artificially-created misalignment of the sensor modules;
the at least one processing unit is configured to identify a corrector function using the measurements of the first radiation that has interacted with the at least one flag; and
the at least one processing unit is configured to adjust the caliper measurement using the corrector function.

17. The system of claim 10, wherein:
the at least one processing unit is configured to obtain initial displacement measurements using the at least one flag;
the at least one processing unit is configured to fit a corrector function to the initial displacement measurements; and
the at least one processing unit is configured to adjust the caliper measurement using the fitted corrector function.

18. The system of claim 17, wherein:
the corrector function comprises one of multiple corrector functions associated with multiple caliper sensors; and
the at least one processing unit is configured to select the corrector function that is associated with a particular one of the caliper sensors.

19. The system of claim 10, wherein the second sensor module further comprises:
a precision slide configured to move the dome;
a stepper motor configured to move the precision slide in order to move the dome; and
a sensor configured to measure movement of the dome.

20. An apparatus comprising:
at least one processing unit configured to
identify a caliper measurement of a sheet of material, the at least one processing unit also configured to adjust the caliper measurement based on a transverse displacement between a first sensor component in a first sensor module and a second sensor component in a second sensor module of a caliper sensor to generate a corrected caliper measurement; and
at least one memory configured to store the corrected caliper measurement
wherein the first sensor module comprises:
a first radiation source configured to direct first radiation towards a first side of the sheet;
a cover having a first aperture configured to allow the first radiation to pass through the cover; and
a Z-sensor configured to measure distance to the second sensor module;
wherein the second sensor module comprises:
a second radiation source configured to direct second radiation towards a second side of the sheet;
a dome having a second aperture configured to allow the second radiation to pass through the dome, the dome providing a target for the Z-sensor; and
at least one holder configured to position at least one flag within the second aperture during standardization or calibration of the caliper sensor, the at least one flag having one or more known characteristics; and
wherein the at least one processing unit is configured to identify the caliper measurement of the sheet using measurements of the first and second radiation that have interacted with the sheet.

21. The apparatus of claim 20, wherein the at least one processing unit is configured to identify the transverse displacement between the first and second sensor components using one or more measurements from at least one displacement sensor.

22. The apparatus of claim 21, wherein the at least one processing unit is configured to adjust the caliper measurement by applying a corrector function that adjusts the caliper measurement based on the identified transverse displacement.

23. The apparatus of claim 22, wherein the at least one processing unit is configured to identify the corrector function.

* * * * *